United States Patent [19]
Rock et al.

[11] Patent Number: 6,039,047
[45] Date of Patent: Mar. 21, 2000

[54] METHOD AND SYSTEM FOR CHANGING THE APPEARANCE OF A CONTROL REGION OF A MEDICAL DEVICE SUCH AS A DIAGNOSTIC MEDICAL ULTRASOUND SYSTEM

[75] Inventors: David A. Rock, Saline; Paul Schmitter, Dexter, both of Mich.; David Castelnuovo, San Francisco, Calif.; Clement James Goebel, III, Ypsilanti, Mich.

[73] Assignee: Acuson Corporation, Mountain View, Calif.

[21] Appl. No.: 09/183,814

[22] Filed: Oct. 30, 1998

[51] Int. Cl.⁷ .................................................. A61B 19/00

[52] U.S. Cl. .......................................... 128/897; 345/112

[58] Field of Search ..................................... 128/898, 922, 128/923, 924; 345/11, 114, 116, 157; 600/300

[56] References Cited

U.S. PATENT DOCUMENTS

5,603,323  2/1997  Pflugrath et al. .
5,715,823  2/1998  Wood et al. .

Primary Examiner—Max Hindenburg
Assistant Examiner—Brian Szmal
Attorney, Agent, or Firm—Brinks Hofer Gilson & Lione

[57] ABSTRACT

A system and method are provided to allow a user to control the appearance of a control region displayed along with a medical image on a medical device. In one preferred embodiment, when the user positions a pointer over a control region, the appearance of the control region ensures readability by a user. When the user positions the pointer away from the control region, the appearance of the control region changes to a less distracting form. In this way, control regions are made easy to read when a user is using the controls and are made less distracting when a user is viewing displayed medical images.

14 Claims, 5 Drawing Sheets

METHOD AND SYSTEM FOR CHANGING THE APPEARANCE OF A CONTROL REGION OF A MEDICAL DEVICE SUCH AS A DIAGNOSTIC MEDICAL ULTRASOUND SYSTEM

BACKGROUND

Medical devices, such as ultrasound imaging systems and medical image review stations, display medical images and are often used in dimly-lit rooms in order to improve the visualization of the displayed images. Many medical devices also display high-luminance user-interface controls that are used in conjunction with the displayed images. While these high-luminance controls are easily readable by a user, they often distracts the user's eyes from the displayed medical images.

SUMMARY

The present invention is defined by the following claims, and nothing in this section should be taken as a limitation on those claims.

By way of introduction, the preferred embodiments described below allow a user to control the appearance of a control region displayed along with a medical image on a medical device. In one preferred embodiment, when the user positions a pointer over a control region, the appearance of the control region ensures readability by a user. When the user positions the pointer away from the control region, the appearance of the control region changes to a less distracting form. In this way, control regions are made easy to read when a user is using the controls and are made less distracting when a user is viewing displayed medical images.

The preferred embodiments will now be described with reference to the attached drawings.

DETAILED DESCRIPTION OF THE PRESENTLY PREFERRED EMBODIMENTS

As used herein, the term "digital medical image" includes, but is not limited to, an ultrasound image as well as an image generated by any of the following modalities: computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy.

Also as used herein, the term "medical device" refers to any device that can display digital medical images. Medical devices include, but are not limited to, medical image acquisition devices, such as an ultrasound imaging system, and medical image review stations.

Figure 1:
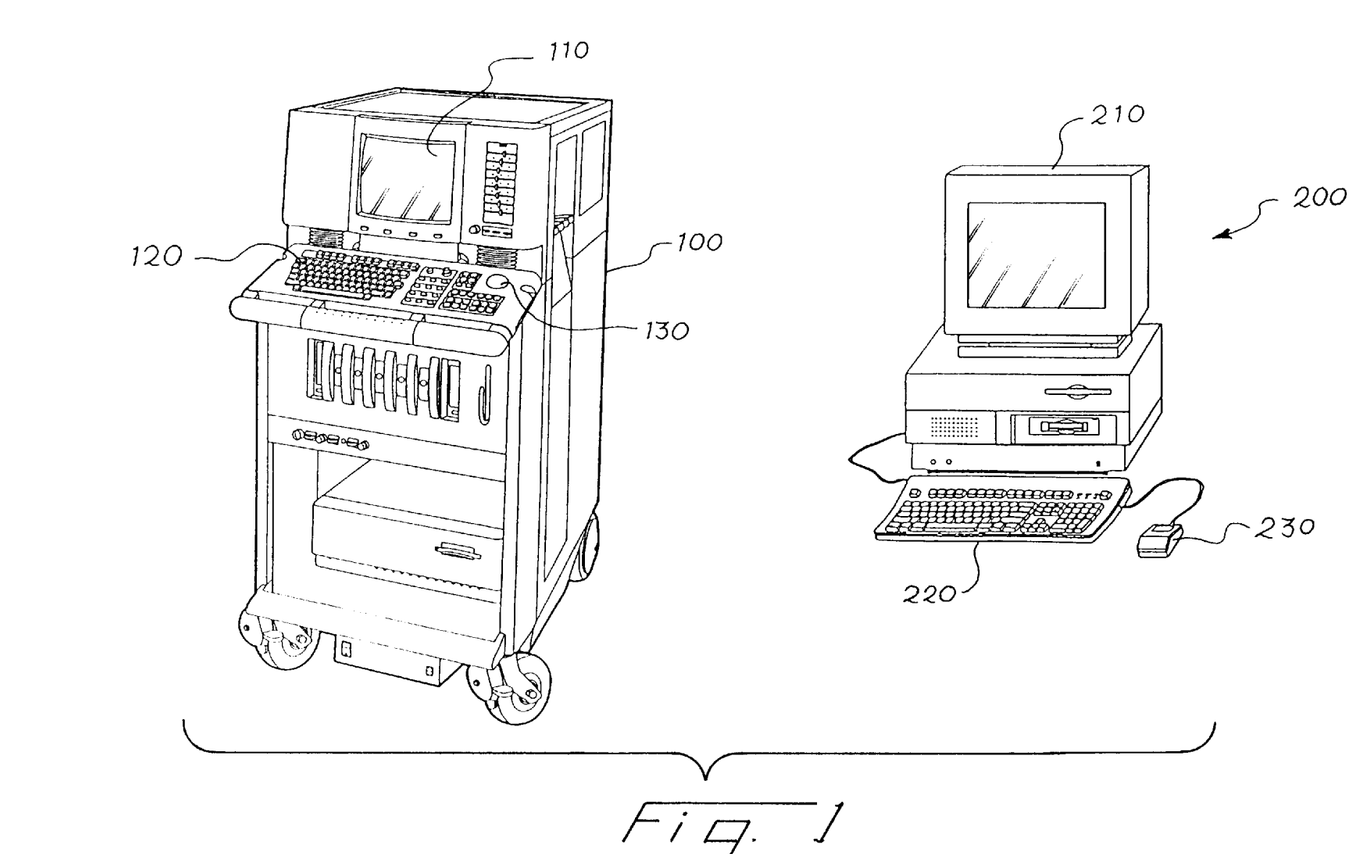
FIG. 1 is an illustration of an ultrasound imaging system and an image review station of a preferred embodiment.

Turning now to the drawings, FIG. 1 is an illustration of two medical devices that can be used with the presently preferred embodiments: an ultrasound imaging system 100 and a medical image review station 200. Generally, a medical device includes a display device 110, 210 and a pointing device to manipulate a pointer (such as an arrow) displayed on the display device 110, 210. The term "pointing device" is intended to encompass any suitable device for manipulating the pointer on the display device 110, 120 and includes a keyboard 120, 220, trackball 130, mouse 230, touch pad, touch screen, and light pen. The pointing device can be physically incorporated into the medical device, such as the trackball 130 in the ultrasound imaging system 100, or can be a separate component, such as the mouse 230 in the medical image review station 200.

The medical device is operative to display a medical image and a control region on the display device 110, 210. As used herein, the term "control region" refers to an area of the display device 110 that is associated with a function that can be performed in conjunction with a medical image. Functions that can be associated with control regions include, but are not limited to, presenting next/previous medical images, loading patient data associated with a medical image, printing a medical image, changing the display format of a medical image, indicating whether a medical image has been reviewed, deleting a medical image, archiving a medical image, editing a medical image, and accessing other display screens. The user can select a control region, for example, by positioning a pointer over the control region and indicating a selection (e.g., clicking a mouse button) or by merely positioning the pointer over the control region. Images (such as a symbol or icon) and/or text can be displayed in the control region to allow the user to identify which function will be performed upon selection of the control region.

Figure 2:
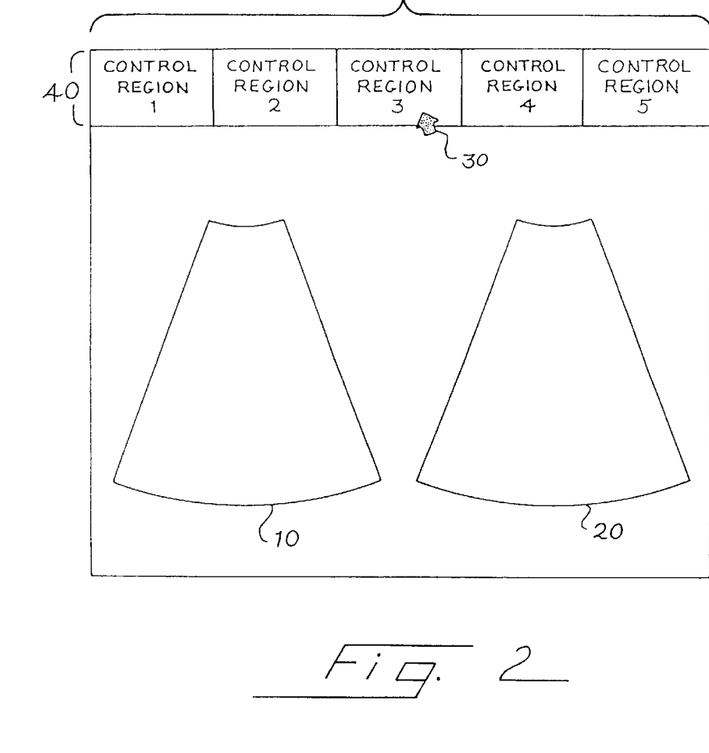
FIG. 2 is an illustration of a screen display of a preferred embodiment in which a pointer is positioned over a control region.

FIG. 2 is an illustration of a screen generated on the display device by an application running in the medical device. As shown in FIG. 2, this screen displays two medical images 10, 20, a pointer 30, and a toolbar 40 containing control regions 1–5. As discussed in the Background section above, the appearance of the control regions can be distracting to a user when he is studying the displayed images 10, 20. To remove this distraction, the medical device is equipped with an appearance-control application that changes the appearance of the control regions in response to the position of the pointer 30. It is preferred that the appearance-control application be implemented with software and that the medical device comprise the necessary hardware (such as a CPU) to execute the software. Of course, any appropriate software language, preferably C++, and any appropriate hardware, analog or digital, can be used.

Additionally, all of the functionality can be implemented exclusively with hardware.

Figure 3:
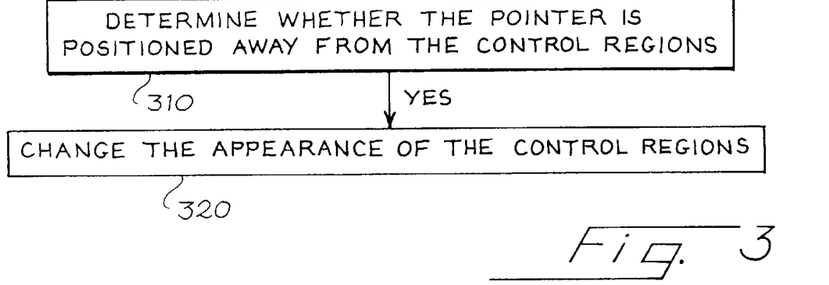
FIG. 3 is a flow chart of a method of a preferred embodiment for changing the appearance of a control region of a medical device.

The flow chart of FIG. 3 illustrates the operation of the appearance-control application. As shown in this flow chart, the appearance-control application first compares the position of the pointer, which can be provided by the medical device's operating system, with the location of the control regions to determine whether the pointer is positioned away from the control regions (310). If the pointer is positioned away from the control regions, the appearance-control application changes the appearance of the control regions (320). The following examples will illustrate the operation of this method.

Figure 4:
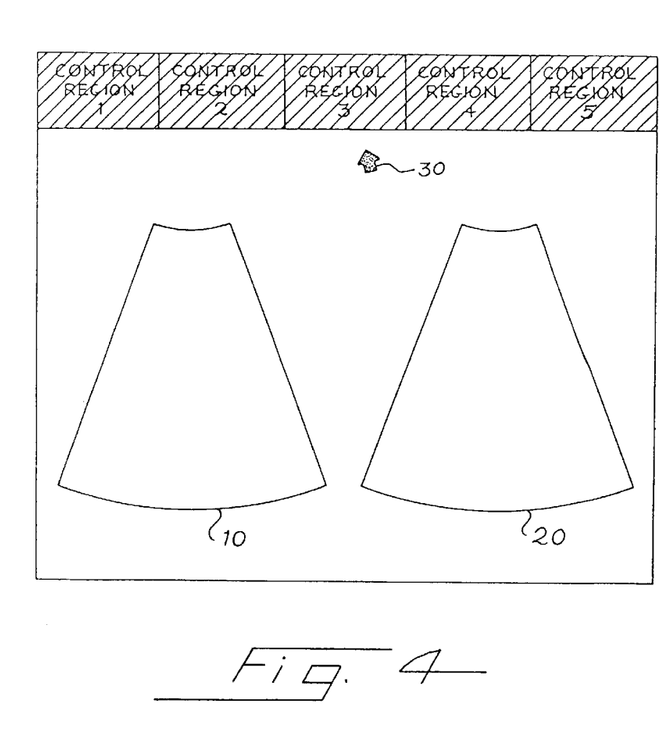
FIG. 4 is an illustration of a screen display of a preferred embodiment in which a pointer is positioned away from a control region and the appearance of each control region is changed.

When a user is using (e.g., viewing or selecting) a control region, he positions the pointer 30 over one of the control regions, and the appearance of the control regions preferably allows the user to clearly and easily discern the control regions on the display screen, as shown in FIG. 2. When a user is studying a displayed medical image 10, 20, however, the appearance of the control regions can make the medical image 10, 20 difficult to view. To change the appearance of the control regions to a less distracting form, the user moves the pointer 30 away from the control regions, as shown in FIG. 4. When the appearance-control application determines that the pointer 30 is positioned away from the control regions, it changes the appearance of the control regions to make the control regions less distracting to the user. When the user wants to use the control regions again, he simply returns the pointer 30 over one of the control regions, and the appearance-control application returns the control regions to their original appearance (i.e., the appearance shown in FIG. 2).

As described above, when the user moves the pointer 30 away from the control regions, the appearance-control application changes the appearance of the control regions. There are several techniques that can be used to accomplish this. Preferably, the appearance-control application changes the appearance of the control regions by changing the luminance of the control regions. The medical device can use the H-S-B (Hue-Saturation-Brightness) color model to represent a color pixel on the display device. In the H-S-B color model, a pixel's luminance is represented by its B (Brightness) value, which ranges from 0 to 100. Preferably, the appearance-control application reduces the luminance value of the control regions by 50% when the user positions the pointer 30 away from the control regions (e.g., a B value of 80 is reduced to 40). In this way, when the user positions the pointer 30 over the control regions, the control regions appear in a "normal" state, and when the user moves the pointer 30 away from the control regions, the control regions appear in a "dimmed" state.

Figure 5:
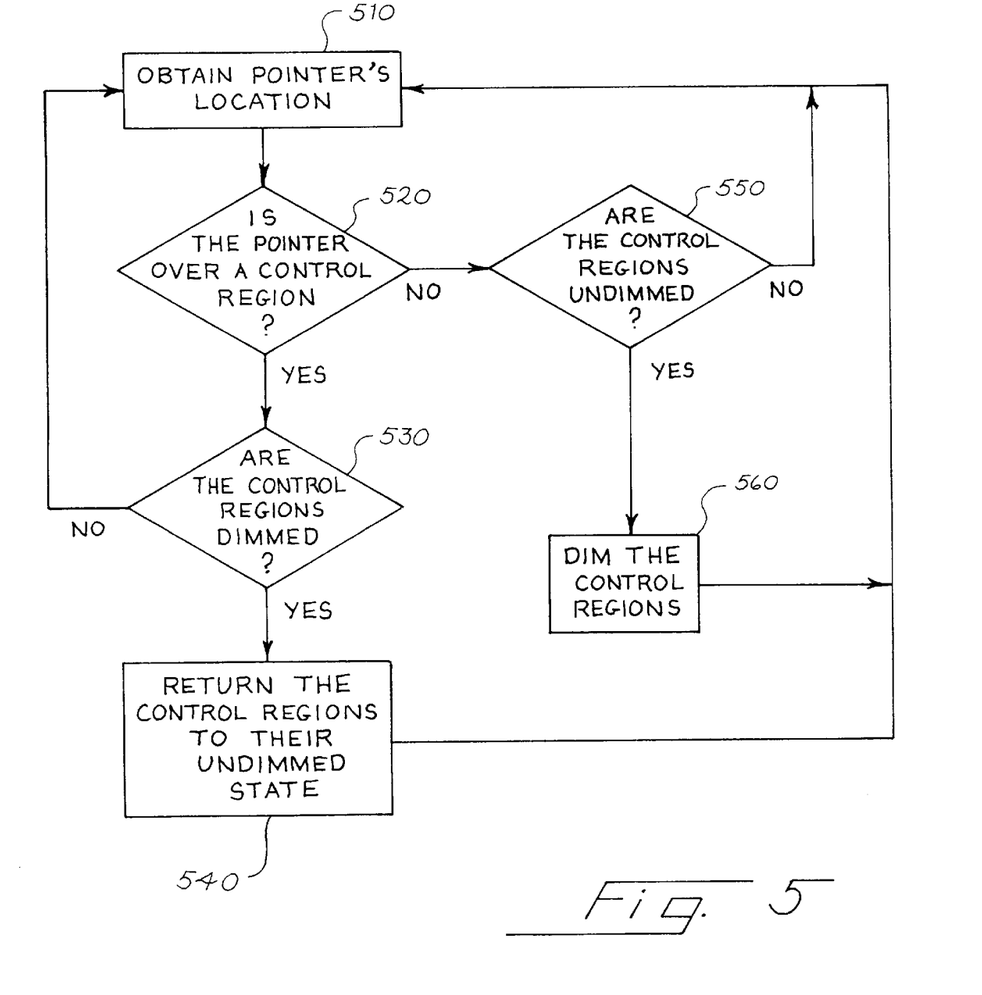
FIG. 5 is flow chart of a method of a preferred embodiment for changing the luminance of a control region of a medical device.

FIG. 5 is a flow chart of a preferred method for reducing the luminance of a control region. First, the pointer's location is obtained (510), and then the appearance-control application determines if the pointer is over a control region (520). If the pointer is over a control region, the control-appearance application then determines if the control regions are dimmed (530). If the control regions are undimmed, no action is taken, and the control-appearance application waits for the next pointer movement. If the control regions are dimmed, the control-appearance application returns the control regions to their undimmed state (540). Similarly, if the pointer is not over a control region, the control-appearance application determines if the control regions are undimmed (550). If the control regions are undimmed, the control-appearance application dims the control regions (560); otherwise, the control-appearance application takes no action and waits for the next pointer movement. Table 1 lists pseudo-code that embodies one form of the method described above.

Figure 6:
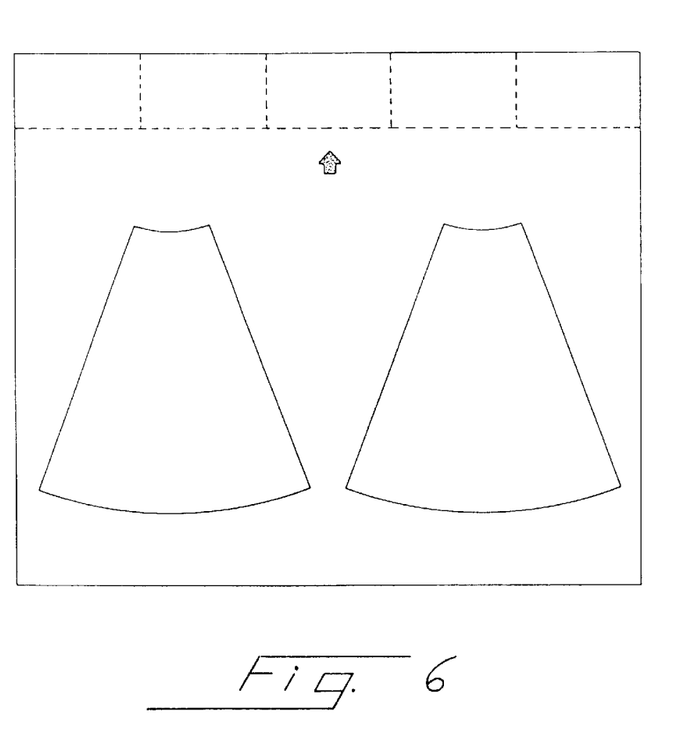
FIG. 6 is an illustration of a screen display of a preferred embodiment in which control regions are hidden from view.

The appearance-control application can change the appearance of the control regions in other ways. For example, instead of merely changing the brightness of the control regions, the appearance-control application can change the color of the control regions to make them less distracting to a user (e.g., changing the color of a control region from an alarming red to a soothing gray). The appearance-control application can also change the size or shape of the control regions (e.g., reducing the size of the control regions to make them less of a distraction). Additionally, the appearance-control application can invert the appearance of two areas of a control region. For example, the appearance-control application can invert the color of the background with the color of the text of a control region (e.g., black text on a white background to white text on a black background). Further, the appearance-control application can change the appearance of the control regions by hiding the control regions from the user, as shown in FIG. 6. Although the control regions are not visible to the user, the appearance-control application will recognize when the pointer 30 is positioned in the area of the screen that formerly displayed the control regions. When the pointer 30 returns to this area, the appearance-control application again displays the control regions to the user. Because novice users may not know how to access hidden control regions, it may be preferred to use another technique that allows the control regions to be visible without being a distraction.

Figure 7:
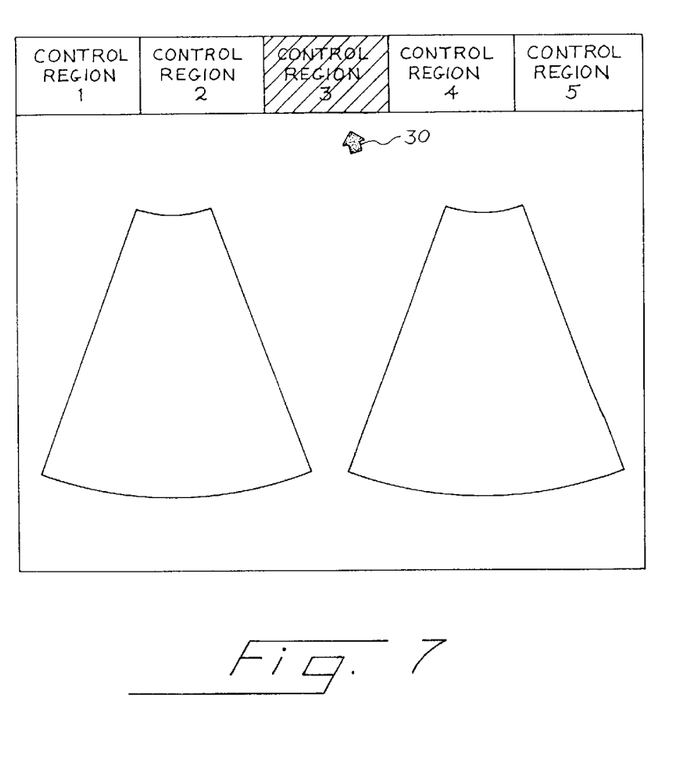
FIG. 7 is an illustration of a screen display of a preferred embodiment in which the appearance of only one control region is changed.
Figure 8:
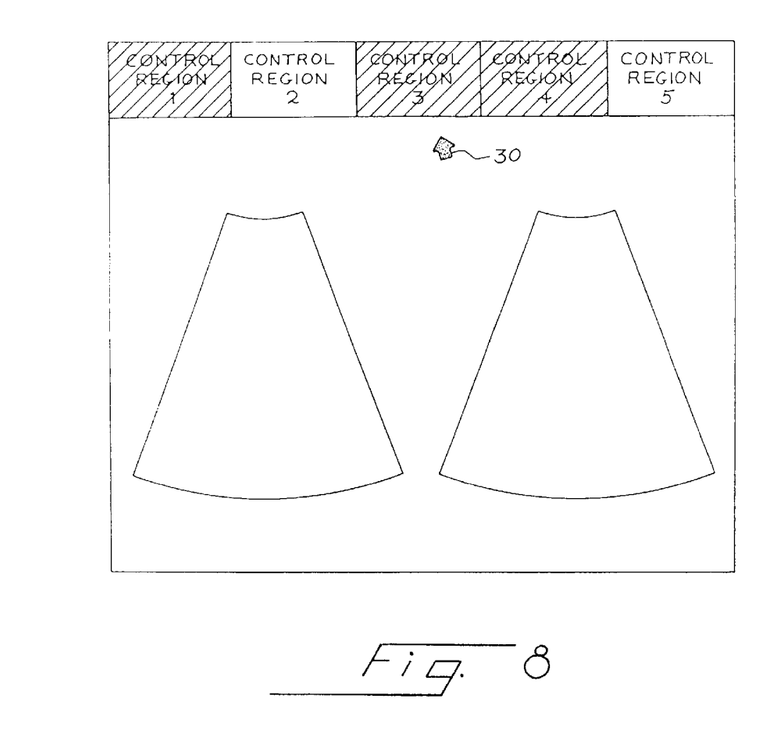
FIG. 8 is an illustration of a screen display of a preferred embodiment in which the appearance of only control regions 1, 3, and 4 are changed.
Figure 9:
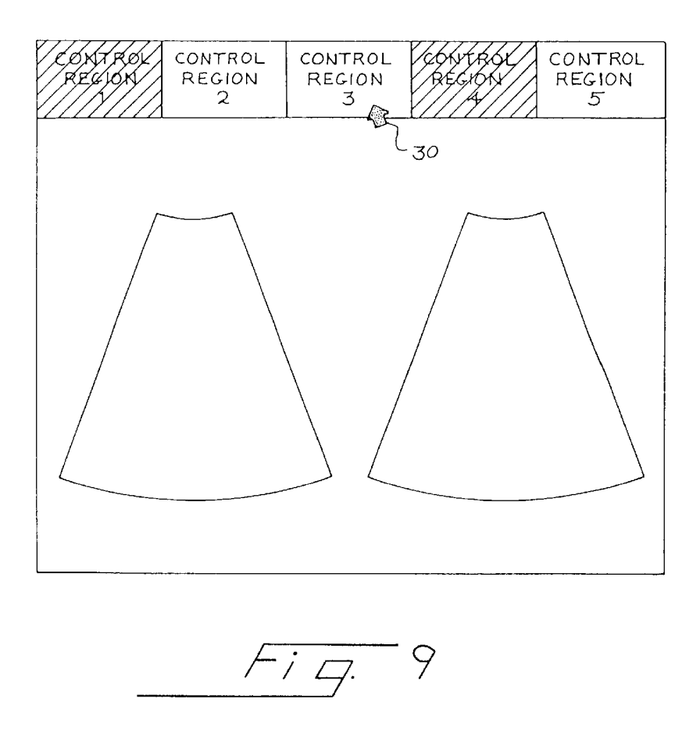
FIG. 9 is an illustration of a screen display of a preferred embodiment in which only the control region selected by a pointer returns to its original appearance.

There are several alternatives to the embodiments described above. In the preferred embodiment discussed above in conjunction with FIG. 4, the appearance-control application changed the appearance of every control region in response to the pointer 30 being either over or away from any one of the control regions. In another preferred embodiment, the appearance-control application changes the appearance of only the control region over which the pointer was previously located. For example, in FIG. 2, the pointer 30 is positioned over control region 3. When the user moves the pointer 30 away from control region 3, the appearance-control application changes the appearance of control region 3 without changing the appearance of the other control regions, as shown in FIG. 7. When the user returns the pointer 30 over control region 3 (or, alternatively, over any of the control regions), control region 3 returns to its original appearance shown in FIG. 2. In another preferred embodiment, the appearance-control application changes the appearance of some, but not all, of the control regions when the pointer 30 is moved. For example, when the user moves the pointer 30 away from control region 3 in FIG. 2, the appearance-control application can change the appearance of control regions 1, 3, and 4 but not control regions 2 and 5, as shown in FIG. 8. When the user returns the pointer 30 over control region 1, 3, or 4 (or, alternatively, over any of the control regions), control regions 1, 3, and 4 return to their original appearance shown in FIG. 2. Alternatively, only some of the control regions return to their original appearance. In FIG. 9, for example, only the control region over which the user returns the pointer 30 is returned to its original appearance. In yet another alternative, when the pointer returns to a control region, the appearance-control application returns another control region, but not the control region over which the pointer is currently located, to its original appearance.

It is important to note that one or more of the preferred embodiments described above can be used in combination.

For example, when a user moves the pointer away from the control regions, the appearance-control application can dim control regions 1 and 2, change the size of control regions 3 and 4, and hide control region 5 from view. Additionally, the degree of appearance changes can vary. For instance, in the preceding example, the appearance-control application can dim control region 1 more than control region 2. In another alternative, instead of returning the control regions to their original appearance, the appearance-control application can change some or all of the control regions to a different appearance. For example, some or all of the control regions can become brighter than their original state after returning from their dimmed state.

In another alternative embodiment, the appearance of the control regions change to become more—not less— noticeable to the user. For example, instead of reducing the size of the control regions when the pointer is positioned away from the control regions, the appearance-control application can increase the size of the control regions.

It is intended that the foregoing detailed description be understood as an illustration of selected forms that the invention can take and not as a definition of the invention. It is only the following claims, including all equivalents, that are intended to define the scope of this invention.

TABLE 1

```
ProgramStart
/* Beginning of program */
{
    /* Initialize global variables */
    Execute Initialize Variables
    /* Continue to monitor mouse movement until the program ends */
    Run until the program ends
    {
        Execute WaitForCursorMove
    }
}
Initialize Variables
/* Routine to initialize global variables */
{
    ControlFadeMaximum = 1.0;/* Full luminous value (normal brightness) */
    ControlFadeMinimum = 0.5;/* 50% luminous value (dimmed brightness) */
    ControlRedrawTime = 10;  /* Time interval (in milliseconds) for redrawing
control */
    MaxFadeTime = 100;    /* Max time (in milliseconds) to fade control */
    ExpiredFadeTime = 0; /* Amount of time (in milliseconds) expired during
fade process */
    ControlFadeValue = 1.0; /* Current fade value (open between 1.0 and 0.5)
for control */
    TimerID = 0;      /* ID assigned to routine that get called
periodically */
}
WaitForCursorMove
/* Gets called when the cursor is moved, initiates dimming and brightening */
{
    /* Check to see if the cursor was moved over a control */
    If the cursor just moved over a control
    {
        /* If we are currently dimming a control, stop the operation */
        /* The operating system provides this capability */
        TerminateTimerRoutine(TimerID)
        /* Brighten the control */
        Execute FadeUp
    }
    /* Check to see if the cursor was moved away from a control */
    If the cursor just moved away from a control
    {
        /* If we are currently dimming a control, stop the operation */
        /* The operating system provides this capability */
        TerminateTimerRoutine(TimerID)
        /* Dim the control */
        Execute InitiateFadeDown
    }
}
InitiateFadeDown
/* Initiates the control dimming operation */
{
    /* Initialize ExpiredFadeTime to MaxFadeTime */
    ExpiredFadeTime = MaxFadeTime;
    /* Dim the control */
    Execute FadeDown
}
FadeDown
/* Performs dim operation on a control */
{
    /* Update expired fade time */
    ExpiredFadeTime = ExpiredFadeTime − ControlRedrawTime;
    /* If it is less than 0, set it to 0 */
```

TABLE 1-continued

```
    if ExpiredFadeTime is less than 0
        ExpiredFadeTime = 0;
    /* Calculate the control fade value */
    Execute CalculateControlFadeValue
    /* Redraw the control to reflect the new brightness value */
    Execute RedrawControl
    /* If appropriate, set a timer to execute FadeDown again */
    /* The operating system provides this capability */
    if ExpiredFadeTime is greater than 0
        TimerID = InstallTimerRoutine(FadeDown, ControlRedrawtime)
}
InitiateFade Up
/* Initiates the control brightening operation */
{
    /* Initialize ExpiredFadeTime to 0 */
    ExpiredFadeTime = 0;
    /* Brighten the control */
    Execute FadeUp
}
FadeUp
/* Performs brighten operation on a control */
{
    /* Update expired fade time */
    ExpiredFadeTime = ExpiredFadeTime + ControlRedrawTime;
    /* If it is greater than MaxFadeTime, set to MaxFadeTime */
    if ExpiredFadeTime is greater than MaxFadeTime
        ExpiredFadeTime = MaxFadeTime;
    /* Calculate the control fade value */
    Execute CalculateControlFadeValue
    /* Redraw the control to reflect the new brightness value */
    Execute RedrawControl
    /* If appropriate, set a timer to execute FadeUp again */
    /* The operating system provides this capability */
    if ExpiredFadeTime is less than MaxFadeTime
        TimerID = InstallTimerRoutine(FadeUp, ControlRedrawTime)
}
CalculateControlFadeValue
/* Calculates new ControlFadeValue based upon the value of ExpiredFadeTime */
{
    ControlFadeValue = ControlFadeMinimum + ((ControlFadeMaximum –
        ControlFadeMinimum) * (ExpiredFadeTime/
        MaxFadeTime))
}
RedrawControl
/* Redraws a control to reflect a new brightness setting */
{
    /* Calculate new brightness value based upon ControlFadeValue */
    NewBrightnessValue = OriginalBrightnessValue * ControlFadeValue
    /* Convert HSB color value to RGB color value */
    /* The operating system provides this capability */
    HSBToRGB(OriginalHueValue, OriginalSaturationValue,
NewBrightnessValue, RedValue, GreenValue, BlueValue);
    /* Use the RGB color value to draw the control */
}
```

What is claimed is:

1. In a medical device comprising a display device, an application operative to display a medical image and a plurality of control regions on the display device, and a pointer device operative to position a pointer on and away from one of said plurality of control regions; a method for changing the appearance of at least two of said plurality of control regions, the method comprising:

(a) determining whether the pointer is positioned away from said plurality of control regions; and then (b) changing the appearance of at least two of said plurality of control regions in response to the pointer being positioned away from said plurality of control regions.

2. The method of claim 1, wherein (b) comprises changing the luminance of at least two of said plurality of control regions in response to the pointer being positioned away from said plurality of control regions.

3. The method of claim 1, wherein (b) comprises reducing the luminance of at least two of said plurality of control regions in response to the pointer being positioned away from said plurality of control regions, thereby making the at least two of said plurality of control regions less distracting to a user viewing said medical image on said display device.

4. The method of claim 1, wherein (b) comprises changing the color of at least two of said plurality of control regions in response to the pointer being positioned away from said plurality of control regions.

5. The method of claim 1, wherein (b) comprises changing the color of at least two of said plurality of control regions to make the at least two of said plurality of control regions less distracting to a user viewing said medical image on said display device, in response to the pointer being positioned away from said plurality of control regions.

6. The method of claim 1, wherein a control region comprises a first area characterized by a first appearance and a second area characterized by a second appearance, and wherein (b) comprises inverting the first and second appearances in response to the pointer being positioned away from said plurality of control regions.

7. The method of claim 1, wherein a control region comprises a first area characterized by a first color and a second area characterized by a second color, and wherein (b) comprises inverting the first and second colors in response to the pointer being positioned away from said plurality of control regions.

8. The method of claim 1, wherein a control region comprises a first area characterized by a first appearance and a second area characterized by a second appearance, and wherein (b) comprises inverting the first and second appearances to make the at least two of said plurality of control regions less distracting to a user viewing said medical image on said display device, in response to the pointer being positioned away from said plurality of control regions.

9. The method of claim 1, wherein (b) comprises changing the size of at least two of said plurality of control regions in response to the pointer being positioned away from said plurality of control regions.

10. The method of claim 1, wherein (b) comprises reducing the size of at least two of said plurality of control regions in response to the pointer being positioned away from said plurality of control regions, thereby making the at least two of said plurality of control regions less distracting to a user viewing said medical image on said display device.

11. The method of claim 1, wherein (b) comprises removing at least two of said plurality of control regions from the display device in response to the pointer being positioned away from said plurality of control regions.

12. The method of claim 1, wherein (b) comprises changing the appearance of at least two of said plurality of control regions from a first appearance to a second appearance in response to the pointer being positioned away from said plurality of control regions, and wherein the method further comprises:

(c) determining whether the pointer is positioned over one of said plurality of control regions; and then (d) changing the appearance of the at least two of said plurality of control regions from the second appearance to the first appearance in response to the pointer being positioned over one of said plurality of control regions.

13. In a medical device comprising a display device, an application operative to display a medical image and a plurality of control regions on the display device, and a pointer device operative to position a pointer on and away from one of said plurality of control regions, the improvement comprising:

first means for determining whether the pointer is positioned away from said plurality of control regions; and second means for changing the appearance of at least two of said plurality of control regions in response to the pointer being positioned away from said plurality of control regions.

14. A computer usable medium having computer readable program code embodied therein for use in a medical device comprising a display device, an application operative to display a medical image and a plurality of control regions on the display device, and a pointer device operative to position a pointer on and away from one of said plurality of control regions; the computer readable program code comprising:

first computer readable program code operative to determine whether the pointer is positioned away from said plurality of control regions; and second computer readable program code operative to change the appearance of at least two of said plurality of control regions in response to the pointer being positioned away from said plurality of control regions.

* * * * *

UNITED STATES PATENT AND TRADEMARK OFFICE
CERTIFICATE OF CORRECTION

PATENT NO. : 6,039,047
DATED : March 21, 2000
INVENTOR(S) : David A. Rock et al.

It is certified that error appears in the above-identified patent and that said Letters Patent is hereby corrected as shown below:

In column 1, line 14, delete "distracts" and substitute --distract-- in its place.

In column 2, line 25, delete "120" and substitute --210-- in its place.

In column 4, line 45, delete "(or." and substitute --(or,-- in its place.

In column 7, line 12, delete "ControlRedrawtime" and substitute --ControlRedrawTime-- in its place.

In column 7, line 14, delete "InitiateFade Up" and substitute --InitiateFadeUp-- in its place.

Signed and Sealed this

Twenty-fourth Day of April, 2001

Attest:

NICHOLAS P. GODICI

*Attesting Officer*    Acting Director of the United States Patent and Trademark Office